United States Patent [19]

Dolkart et al.

[11] Patent Number: 4,574,085

[45] Date of Patent: Mar. 4, 1986

[54] METHOD FOR USING DIALYSIS SOLUTION CONTAINING GLYCEROL

[75] Inventors: Ralph E. Dolkart, Brugge, Belgium; Nicholas J. Kartinos, Park Ridge, Ill.

[73] Assignee: Baxter Travenol Laboratories, Inc., Deerfield, Ill.

[21] Appl. No.: 263,818

[22] Filed: May 15, 1981

[51] Int. Cl.[4] .................. A61K 31/70; A61K 31/195; A61K 33/06; A61K 33/14; A61K 33/22

[52] U.S. Cl. .................... 424/148; 424/153; 424/154; 514/23; 514/561

[58] Field of Search ............... 424/153, 154, 180, 319, 424/148; 514/23, 561

[56] References Cited

U.S. PATENT DOCUMENTS

| | | | |
|---|---|---|---|
| 3,234,089 | 2/1966 | McQuarrie | 167/58 |
| 3,793,450 | 2/1974 | Schnell | 424/180 |
| 3,897,550 | 7/1975 | Reynolds | 424/153 |
| 3,950,529 | 4/1976 | Fischer et al. | 424/319 |
| 3,968,205 | 7/1976 | Bickel | 424/153 |
| 4,005,190 | 1/1977 | Mader et al. | 424/319 |
| 4,164,568 | 8/1979 | Bywater | 424/153 |

OTHER PUBLICATIONS

Helen Burch et al., *Journal of Biological Chemistry*, vol. 245, pp. 2092–2102 (1970).
Finckh, *Journal of Pathological Bacteriology*, vol. 78, pp. 197–202 (1959).
Physicians' Desk Reference 28th Edition, 1974, p. 1257.
The Merck Index, 9th Edition, 1976, Compound No. 4319.

*Primary Examiner*—Stanley J. Friedman
*Attorney, Agent, or Firm*—Paul C. Flattery; Garrettson Ellis

[57] ABSTRACT

A dialysis solution, typically a peritoneal dialysis solution, comprises a water solution of physiological pH, having physiological salts and glycerine present in concentrations sufficient to safely effect the removal of solutes and water from a patient by peritoneal dialysis.

14 Claims, No Drawings

METHOD FOR USING DIALYSIS SOLUTION CONTAINING GLYCEROL

TECHNICAL FIELD

The medical procedure known as continuous ambulatory peritoneal dialysis (CAPD) is rapidly growing in clinical acceptance as the technique of choice for maintaining many patients who have lost or compromised kidney function. Peritoneal dialysis solution is inserted in the peritoneal cavity, whereby diffusion exchange takes place between the solution and the bloodstream across the natural body membranes, to remove by diffusion the waste products which are normally excreted through the kidneys, typically solutes such as sodium and chloride ions and other matierals normally excreted as urine by the body such as urea and creatinine, and also water.

The nature and rate of the materials removed from the body of peritoneal dialysis is a function of the solutes present in the peritoneal dialysis solution. Physiological salts are present in the peritoneal dialysis solution such as sodium chloride, calcium chloride, sodium lactate, and sodium acetate, generally at slightly hypotonic concentrations (but for calcium) so that excess concentrations of the ions forming such salts in the bloodstream will diffuse into the peritoneal dialysis solution for removal.

BACKGROUND ART

To remove water from the patient, as is generally necessary, other solutes may be added to generate the necessary osmotic pressure. Typically, this solute is a sugar such as glucose, which may normally be present in peritoneal dialysis solutions in a concentration of at 0.5 to 4.25 percent (wt/vol.). When it is desired to increase the ultrafiltration of water from the patient, higher concentrations of sugar in that range are used.

However, as a disadvantage of this system for inducing ultrafiltration, during the peritoneal dialysis procedure, as water diffuses into the peritoneal dialysis solution, sugar present in the peritoneal dialysis solution diffuses into the bloodstream to a significant extent. Accordingly, while the system is safe and effective for increasing the ultrafiltration during peritoneal dialysis, the patient receives a heavy dose of calories during each peritoneal dialysis procedure from the sugar diffusing into his bloodstream. In many instances, this high caloric dose is undesired, as it can result in weight gain and fat. Particularly in the case of diabetics, the transport of significant quantities of a sugar such as glucose or fructose from the peritoneal dialysis solution into the patient's bloodstream can create complications in the medical maintenance of the patient.

Glycerol, which is a sugar alcohol, has been added on an experimental basis to glucose-containing hemodialysis solution in which the dialysis solution is directly dialyzed with an artificial membrane against blood. See the articles by Arieff et al., *Kidney International*, Volume 14 (1978) pages 270–278, and Van Stone et al., *Transactions of the Americal Society for Artificial Internal Organs*, Volume 25 (1979) pages 354–356. The purpose of such addition of glycerol was in an attempt to reduce the incidence of "disequilibrium syndrome", which is believed to result from the reduction of plasma osmolality relative to the osmolality of cell interiors due to the hemodialysis procedure. According to the latter article, the presence of glycerol was unsuccessful in reducing the symptoms of disequilibrium syndrome.

Also, the polyalcohol sorbitol has been used in peritoneal dialysis solutions. However, sorbitol proved to be toxic under certain conditions of chronic use, due to the creation of a hyperosmolar state, which naturally severely limited its utility.

DISCLOSURE OF INVENTION

In accordance with this invention, a dialysis solution is provided which comprises a water solution of physiological pH, for example pH 5 to 7.4, and preferably pH 5.6 to 7.2. The solution of this invention may have the typical physiological salts which are commonly found in conventional dialysis solutions, plus glycerol, present in concentrations sufficient to safely effect the removal of solutes and water from a patient by peritoneal dialysis. Typically, the solution is used in peritoneal dialysis, although it may also be used in hemodialysis.

Preferably, the glycerol (glycerine) is utilized in the dialysis solution as a partial or preferably complete substitute for a sugar such as dextrose, resulting in various significant advantages.

First, the substitution of a sugar by glycerol in a peritoneal dialysis solution reduces the body load of such sugar. This reduces the possibility of elevated triglycerides in the patients, who typically have a chronic and continued requirement for peritoneal dialysis, and thus by the prior art are receiving constant, high loads of sugar in the peritoneal dialysis solution in order to provide enough osmolality to permit a desired ultrafiltration of water to take place to remove water from a patient's system.

Being of a lower molecular weight than sugars, glycerol can express an osmotic effect at much lower concentrations in terms of weight percent. Because of this, the patient is exposed to a significantly reduced caloric load, since less weight of glycerol present in the solution can provide an equal osmotic effect to that of dextrose, for example. Anhydrous dextrose has a molecular weight of 180, while glycerol has a molecular weight of 92. Thus 180 mg. of dextrose are necessary to provide 1 milliosmol per liter of solution, while only 92 mg. of glycerol are required to provide a milliosmol per liter.

As further advantage, glycerol, being a polyalcohol, does not contain a carbonyl group as do the usual sugars. As a consequence, peritoneal dialysis solutions which are free of sugar, and containing glycerol as a substitute, can be steam sterilized at a higher pH than can solutions containing sugars. Sugars must be typically maintained during sterilization in acid pH ranges of 5 to 5.5, to minimize degradation due to the presence of the carbonyl group in sugars. Such pH ranges are slightly more acidic than is optimum for the ideal peritoneal dialysis solution to maximize the patient's comfort and well being. Irritation within the peritoneal cavity can take place due to the slightly acidic nature of such peritoneal dialysis solution, which, in turn, can increase the chances for peritonitis.

However, solutions free of sugars and containing glycerol may be sterilized in more physiologic pH ranges, for example pH 5.6–7.4, for a better pH for use as a peritoneal dialysis solution.

Glycerol is rapidly and completely metabolized and has been clearly established to be safe. It is particularly advantageous, because a major metabolic route of the glycerol does not require insulin, although a portion of the glycerol is metabolized into glucose and thus requires insulin for further metabolization. The advantage of this is that glycerol is clearly much more easily metabolized by diabetics than an equal weight of glucose. This greatly facilitates the control and maintenance of the diabetic patient who must be maintained with peritoneal dialysis.

Furthermore, the use of glycerol as a substitute for sugars provides practical opportunities for the creation of a peritoneal dialysis solution, or a parenteral solution, which contains not only glycerol but also an amino acid source material such as free amino acids or protein hydrolyzates. Such a solution not only can be utilized to provide normal or elevated osmolarity from both the amino acid source and the glycerol for stimulating ultrafiltration during peritoneal dialysis, but it can also serve as a nutrient solution, being capable of providing total parenteral nutrition by peritoneal dialysis or direct intravenous administration.

The reason for this is that amino acids and (poly)peptides cannot be effectively heat-sterilized in the presence of sugars containing carbonyl groups, because of a chemical reaction that can take place between the amino acids and the carbonyl group. Glycerol, however, is compatible with amino acids and (poly)peptides at higher temperatures, so that the mixed solution can be effectively heat sterilized.

Preferably the peritoneal dialysis solution of this invention may comprise a water solution at a pH of 6.0 to 7.4 containing from 130 to 140 mEq/liter of sodium, 0 to 6 mEq/liter of calcium, 0 to 4 mEq/liter of magnesium, 100 to 140 mEq/liter of chloride, and, if desired, other ions, for example 30 to 40 mEq/liter of bicarbonate precursors such as lactate, acetate, malate, and/or succinate. The above ions may be provided by the addition of conventional physiological salts such as sodium chloride, calcium chloride, sodium lactate, sodium acetate, and traces of other salts such as potassium chloride, magnesium chloride, and the like, added in accordance with the known requirements for proper ion balance in a peritoneal dialysis solution.

The glycerol may be added in a proportion sufficient to provide the desired osmolality or osmolarity, for the desired degree of ultrafiltration. An amino acid source material may substitute for a portion of the glycerol to raise the osmolarity of the peritoneal dialysis solution, but due to its much higher cost it is usually only added in a concentration that provides a desired amount of nutrition to the patient. For example, many patients, particularly pediatric patients on chronic peritoneal dialysis, suffer serious protein loss due to the diffusion of amino acids and (poly)peptides from the blood into the peritoneal dialysis solution. Accordingly, by this invention, such protein loss can be counterbalanced, and a net gain of protein may be provided to the patient during the peritoneal dialysis procedure by the use of an amino acid source material in the peritoneal dialysis solution in accordance with this invention. Such a solution, when glucose-free, may be readily sterilized because of the compatability between glycerol and amino acids at sterilizing temperatures.

It is generally preferable for the osmolarity, relative to water, of the peritoneal dialysis solutions of this invention to be from 272 to 700 milliosmols per liter, preferably 279 to 480 milliosmols per liter.

The bicarbonate precursor acid ions, as well as other acid ions of the Krebs cycle, may be added to also offer advantages in pH control of the peritoneal dialysis solution of this invention. The sodium or potassium salts of such ions, for example, may be used for this purpose, or the free acids.

Sulfhydryl-type antioxidants, for example N-acyl cysteine, may be also added to stabilize the amino acids in the peritoneal dialysis solution of this invention.

Preferably, from 0.5 to 40 grams of glycerol may be present per liter of peritoneal dialysis solution, and preferably 5 to 30 grams per liter, glycerol being a well established, safe and effective food in man.

Sources of amino acid are well known, with protein hydrolyzates and the like being currently available as parenteral solutions. From such a source, the amino acids, if desired, may be added to the peritoneal dialysis solution of this invention.

The amount and types of amino acids used herein may vary, for example 1 to 40 grams per liter and preferably 5 to 30 grams/liter. Amino acid mixtures containing both essential and nonessential amino acids may be used, but differ in their osmolarities. However, assuming no electrolytes are present, a 1 percent amino acid mixture (10 grams/liter) will generate approximately 84 milliosmols/liter of osmotic force. As mixed amino acids are introduced and increased, glycerol levels may be reduced so as to maintain the overall desired osmotic properties of the peritoneal dialysis solution.

With a molecular weight of 92, glycerol at a concentration of 92 mg./liter will exert 1 milliosmol of osmotic force. As a mixture the amino acids are generally assumed to have an average molecular weight of 120. Thus, 120 mg. of amino acids per liter will exert 1 milliosmol of osmotic force. Generally, from 0 to 51.6 gram/liter of amino acids may be employed to provide a range of osmotic force from 0 to 430 milliosmols per liter.

Since glycerol has a smaller molecule than dextrose, it diffuses more rapidly through the body membranes of the peritoneal cavity. However, since only slightly over one-half the weight of glycerol in solution can provide equal osmolarity to a given amount of glucose, the net weight of glycerol which is received into the blood stream of the patient by diffusion is less than the weight of dextrose diffusing into the patient in a peritoneal dialysis procedure, when comparing glycerol peritoneal dialysis solution with a corresponding dextrose peritoneal dialysis solution of equal osmolarity. Thus, the amount of calories diffused into the patient with a glycerol solution is substantially reduced.

The net ultrafiltration of a glycerol peritoneal dialysis solution, compared with a dextrose solution of substantially equal osmolarity over four hours of peritoneal dialysis, is calculated to be about 10 percent less when both solutions have concentrations providing 358.7 milliosmols per kilogram of solution. However, if necessray, the concentration of glycerol can be increased, and the patient will still receive considerably less weight of glycerol into his bloodstream during the four hour peritoneal dialysis procedure than he would with the corresponding dextrose solution.

Glycerol is rapidly metabolized in the body, with a greatly reduced need for insulin when compared with dextrose, so that the peritoneal dialysis solution of this invention is particularly advantageous for use with diabetics. Also, the ultrafiltration rates of the glycerolcontaining peritoneal dialysis solutions of this invention are increased when the solutions contain the desired amino acid source material, which functions both to increase ultrafiltration and to prevent protein loss on the part of the patient, and even to provide a protein nutrient to the patient during the peritoneal dialysis process by diffusion of the amino acids or (poly)peptides into the bloodstream.

DESCRIPTION OF SPECIFIC EMBODIMENTS

Specifically, a peritoneal dialysis solution may be utilized with advantage having the ingredients in the proportions stated, as indicated in the Examples below. The examples and the specification are offered for illustrative purposes only, and are not intended to limit the scope of the invention of the application, which is defined in the claims below.

EXAMPLE 1

A solution for peritoneal dialysis having a relatively low osmolarity of about 279 milliosmols may be prepared by adding, per liter of water, 5.67 grams of sodium chloride, 3.92 grams of sodium lactate, 0.257 gram of calcium chloride dihydrate, 0.152 gram of magnesium chloride hexahydrate, and 0.69 gram of glycerol. The glycerol serves as a substitute for the conventional glucose, having the advantages specified above. The solution must of course be sterilized in conventional manner, as of course must all parenteral solutions.

EXAMPLE 2

A peritoneal dialysis solution having an intermediate level osmolarity of about 330 milliosmols may be prepared by adding, per liter of water, 5.55 grams of sodium chloride, 1.96 grams of sodium lactate, 0.257 gram of calcium chloride dihydrate, 0.152 gram of magnesium chloride hexahydrate, 1.42 grams of sodium succinate, and 5.38 grams of glycerol. This sugar-free solution provides a measure of carbohydrate nutrition to the patient, as well as providing ultrafiltration capability.

EXAMPLE 3

This solution may be used as a peritoneal dialysis solution having a high osmolarity of about 600 milliosmols per liter, offering high ultrafiltration. It may also be used for parenteral nutrition, either by intravenous injection or peritoneal dialysis.

To each liter of water there is added 5.67 grams of sodium chloride, 3.92 grams of sodium lactate, 0.15 gram of potassium chloride, 0.257 gram of calcium chloride dihydrate, 0.152 gram of magnesium chloride hexahydrate, 20.25 grams of glycerol, and 13.2 grams of a mixture of essential and nonessential amino acids including either lysine hydrochloride or lysine acetate. The specific mixture of amino acids may be similar to the blend of amino acids found in Travasol® parenteral solution sold by Travenol Laboratories, Inc. of Deerfield, Ill., or any other conventional blend of amino acids, particularly a balanced blend which is suitable as a nutrient.

The resulting solution (when lysine hydrochloride is used) may contain about 112 mEq of chlorine ion. The osmotic effect of the amount of glycerol present is approximately double the osmotic effect of the amino acid mixture, and they both contribute, along with the salts present, to provide a high osmolarity as specified above.

The above-described solutions may be used as dialysis solutions, or they may be intravenously adminsitered to the patient for parenteral nutrition.

That which is claimed is:

1. A method of performing peritoneal dialysis by inserting into the peritoneal cavity a substantially sugar-free dialysis solution which comprises a water solution of pH 5.6 to 7.4, having physiological salts and glycerin present in concentrations sufficient to safely effect the removal of solutes and water from the patient by diffusion through the peritoneal membrane, said glycerin being present in a concentration of 0.5 to 40 grams per liter; allowing said dialysis solution to dwell in the peritoneal cavity for a period of time sufficient to permit said diffusion of solutes in water; and thereafter removing said dialysis solution from the peritoneal cavity.

2. The method of claim 1 in which said dialysis solution contains an amino acid source material.

3. The method of claim 1 in which said dialysis solution contains from 5 to 30 grams per liter of glycerol.

4. The method of claim 2 in which said dialysis solution contains from 5 to 30 grams per liter of said amino acid source material.

5. The method of claim 1 in which said dialysis solution contains from 130 to 140 MEq/liter of sodium, from 100 to 140 MEq/liter of chloride, from 0 to 6 MEq/liter of calcium, and from 0 to 4 MEq/liter of magnesium.

6. The method of claim 5 in which said solution also contains from 30 to 40 MEq/liter of at least one type of bicarbonate precursor ion selected from the group consisting of lactate, acetate, malate, and succinate.

7. The method of claim 1 in which said dialysis solution has an osmolarity of 272 to 700 milliosmols.

8. The method of claim 1 in which said dialysis solution contains an amount of a sulfhydryl-type antioxidant sufficent to improve the stability of the amino acids of said amino acid source material.

9. A method of performing peritoneal dialysis by inserting into the peritoneal cavity a substantially sugar-free dialysis solution which comprises a water solution of physiological pH, having physiological salts present in concentrations sufficient to safely effect the removal of solutes from the patient through the peritoneal membrane, said solution containing from 0.5 to 40 grams per liter of glycerol to enhance the removal of water from the patient by diffusion through the peritoneal membrane, said dialysis solution having an osmolarity of 272 to 700 milliosmols and a pH of 5 to 7.4.

10. The method of claim 9 in which said dialysis solution contains from 5 to 30 grams per liter of glycerol.

11. The method of performing peritoneal dialysis by inserting into the peritoneal cavity a substantially sugar-free dialysis solution which comprises a water solution of physiological pH, having physiological salts present in concentrations sufficient to safely effect the removal of solutes from the patient by diffusion through the peritoneal membrane, and having from 0.5 to 40 grams per liter of glycerol to enhance the removal of water from the patient by diffusion through the peritoneal membrane, said solution also containing from 5 to 30 grams per liter of an amino acid source material, an osmolarity of 272 to 700 milliosmols, and a pH of 5 to 7.4.

12. The method of claim 11 in which said dialysis solution contains from 5 to 30 grams per liter of glycerol.

13. The method of claim 12 in which said dialysis solution contains an amount of a sulfhydryl antioxidant sufficient to improve the stability of amino acids of said amino acid source material.

14. The method of claim 13 in which said dialysis solution contains from 130 to 140 MEq/liter of sodium, from 100 to 140 MEq/liter of chloride, from 0 to 6 MEq/liter of calcium, from 0 to 4 MEq/liter of magnesium, from 30 to 40 MEq/liter of at least one type of bicarbonate precursor ion selected from the group consisting of lactate, acetate, malate, and succinate.

* * * * *